(12) United States Patent
Fujii

(10) Patent No.: US 6,317,636 B1
(45) Date of Patent: Nov. 13, 2001

(54) INFRARED RAY IRRADIATION APPARATUS AND INFRARED RAY IRRADIATION USED SOURCE THEREIN

(75) Inventor: Yoshiya Fujii, Osaka (JP)

(73) Assignee: Sun Medical Co., Ltd., Osaka (JP)

( * ) Notice: Subject to any disclaimer, the term of this patent is extended or adjusted under 35 U.S.C. 154(b) by 0 days.

(21) Appl. No.: 09/318,308

(22) Filed: May 25, 1999

Related U.S. Application Data

(63) Continuation of application No. 09/018,421, filed on Feb. 4, 1998.

(51) Int. Cl.[7] .......................................................... A61F 2/00
(52) U.S. Cl. .............................. 607/100; 607/91; 607/108
(58) Field of Search ................................ 607/100, 91, 89, 607/90, 108, 88

Primary Examiner—Linda C. M. Dvorak
Assistant Examiner—Jocelyn Debra Ram
(74) Attorney, Agent, or Firm—Muramatsu & Associates

(57) ABSTRACT

An far infrared ray irradiation apparatus having a human body mounting portion, an operable cover portion, and a plurality of infrared ray irradiation sources for achieving an improved performance in medical treatment. The infrared ray irradiation sources irradiate far infrared rays not containing near infrared rays of wavelength less than 4 μm, and each of the far infrared irradiation sources is provided at a position close to the portion of the human body to be irradiated so that a whole human body accommodated in a space formed by the human body mounting portion and the operable cover portion can be uniformly heated to a desired temperature without causing any low temperature burns in the human body.

10 Claims, 5 Drawing Sheets

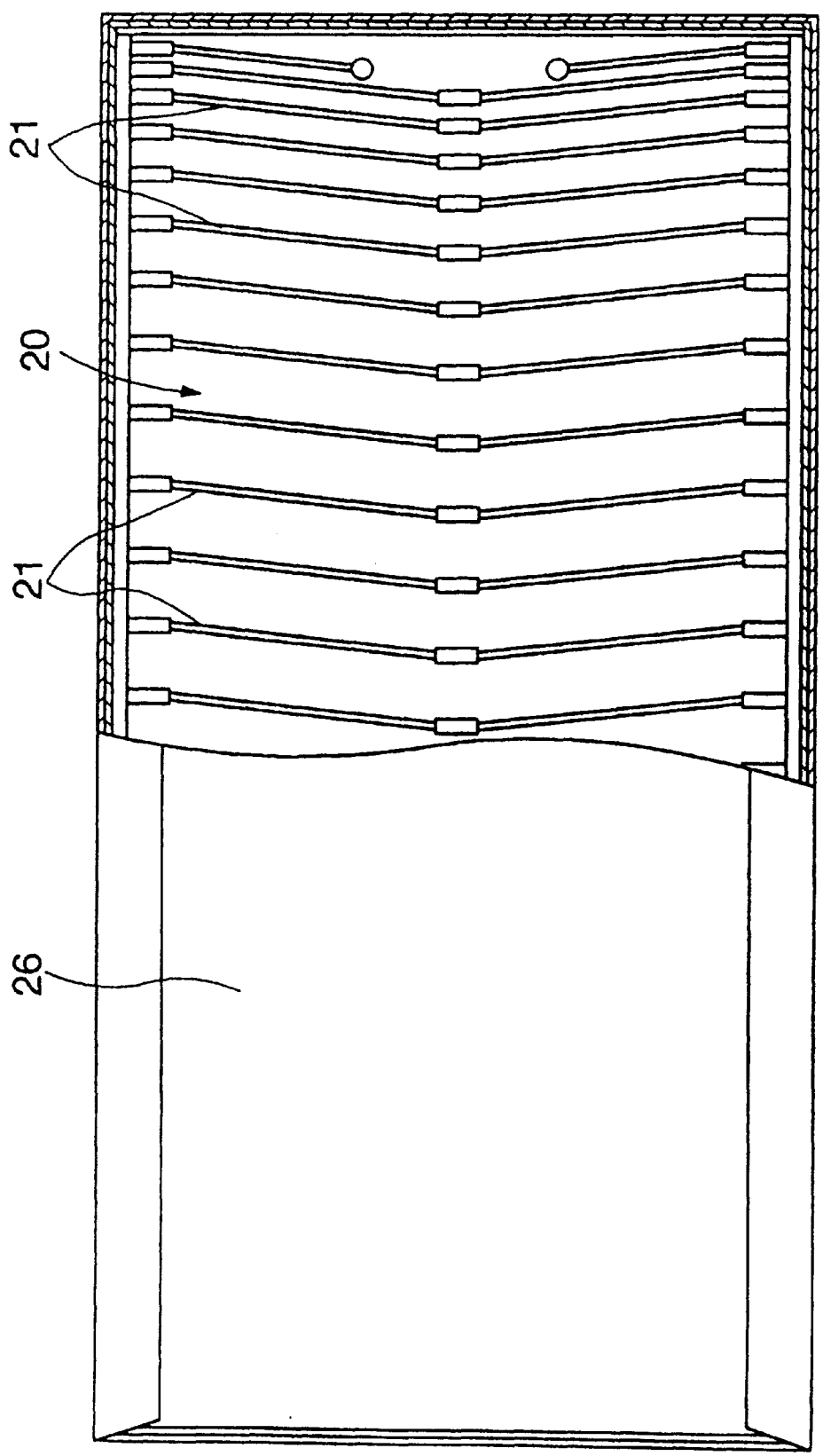

INFRARED RAY IRRADIATION APPARATUS AND INFRARED RAY IRRADIATION USED SOURCE THEREIN

This is a continuation of U.S. patent application Ser. No. 09/018,421 filed Feb. 4, 1998.

BACKGROUND OF THE INVENTION

1. Field of the Invention

The present invention relates to an infrared ray irradiation apparatus and infrared ray irradiation source used therein, and more specifically to an infrared ray irradiation apparatus and infrared ray irradiation source used therein for treating diseases, particularly malignant tumors, viral diseases by irradiating with far-infrared rays and raising the intracorporeal temperature.

2. Description of the Prior Art

Hitherto for malignant tumors such a s cancers, sarcoma, etc., treatments including abscission by operations, irradiation of radioactive ray, administration of drugs, etc. have been given, but tumors which have metastasized are difficult to treat. Even those at the initial stages, operations and other methods may cause excessively large burdens to the human body, lower the immunological competence, and have problems of recurrence of tumors, occurrence of other diseases, etc. Viral diseases are unable to be treated unless suitable vaccine is present, and such is the state of things that there is no effective treatment when people are infected with AIDS virus, etc.

Because in recent years, it has been found that malignant tumors and viruses die out or are inactivated when heated to temperatures exceeding 41° C., hyperthermia has attracted keen attention, and treatments for immersing patients in warm water or methods for irradiating with infused rays have been developed, and infrared ray irradiation apparatus have begun to be fabricated.

However, since the treatment by immersing patients in warm water is achieved by thermal conduction from the human body surface, long time is required for heating the inside of human body, weighing too much on the human body. In addition, the infrared ray irradiation source used for infrared ray irradiation apparatus which have been fabricated and commercially available to date are said to be far infrared ray irradiation source, but in actuality contain a large volume of near infrared rays and has a construction in which the infrared ray irradiation source is formed in a single unit. Near infrared rays have large energy and provide low permeability to human body, and require long time to beat the depth of the human body, and patients must be anesthetized for treatment in order to prevent patients from moving. In addition, because the human body is exposed to infrared ray irradiation source containing near infrared rays for a long time, the energy applied to the body surface increases, and a problem of low-temperature burns occurs, and in order to reduce this problem, an expensive control means must be provided.

In view of the foregoing, it is the main object of this invention to provide an infrared ray irradiation apparatus and infrared ray irradiation source used therein which allow far infrared rays to reach the depth of the human body in a short time, enables optional setting of irradiation intensity for each portion of human body without generating low-temperature burns in patients, and can irradiate far infrared rays only.

SUMMARY OF THE INVENTION

In order to achieve the above-mentioned object, the infrared ray irradiation apparatus according to the present invention comprises a human body mounting portion, an operable cover portion comprising exterior members, interior panels, and members containing filling material between these, and infrared ray irradiation source, wherein this infrared ray irradiation source is arranged more than one to irradiate with far infrared rays not containing near infrared rays with less than 4 µm wavelength, and the periphery of the human body accommodated in a space formed by the human body mounting portion and the cover portion is irradiated with far infrared rays.

It is desirable that the said operable cover portion is designed to be a semi-cylindrical form.

It is desirable that the infrared ray irradiation sources arranged more than one radiate far infrared rays of wavelength from 5 to 20 µm, more suitably from 8 to 15 µm. When the wavelength of far infrared rays radiated from the infrared ray irradiation apparatus is short wavelength of 5 to 20 µm, the temperature of each portion of the body is uniformly raised to the range required for treatment of diseases and is free of localized or excessive temperature rise. In addition, the energy applied to the human body surface does not rise as is the case when the infrared ray irradiation source containing near infrared rays is used, and consequently, there is no fear of generating low-temperature bums by heating the human body surface portion. And as a result of the whole human body heated uniformly, a control for measuring temperature of each body portion and feeding back the data are no longer required or can be simplified. In addition, the far infrared rays of long wavelength reach the depth of the human body, enabling treatment in a short time. Consequently, there is no need for anesthetizing patients before irradiation for treatment, and low-cost and safe treatments can be achieved.

In the case of this invention, since more than one said far infrared ray irradiation sources are arranged, it is possible to set radiation intensity for each irradiation source, and at the required portion, for example, where the distance from the affected portion or body surface to the central portion is large, the radiation intensity can be set high and irradiation time can be set long, and for other portions, irradiation can be set weak and short. Consequently, the use of the apparatus according to this invention no longer requires an expensive control as required by the conventional apparatus.

The other characteristic of this invention is that the far infrared ray irradiation source is installed to the human body mounting surface as in the case of interior panel. With this configuration, it is possible to irradiate the human body with far infrared rays from the overall periphery without rotating the human body during treatment, which contributes to uniform and rapid heating of whole human body and enables shortening of treatment time.

For the far infrared ray irradiation source used for this invention, it is preferable to arrange more than one sources whose size is smaller than that of the said human body mounting portion and interior panel. For the shape, circular, rhombic, square, and other various shapes can be used and are not particularly limited, but in view of the ease of fabrication and arrangement, the irradiation source with a rectangular radiation surface is preferable.

The far infrared ray irradiation source used for this invention has a construction with an inorganic-system material layer generating far infrared rays mounted on the heater surface, and for such inorganic system materials, alumina system, zirconia system, etc. are known and applicable.

This kind of infrared ray irradiation sources are preferably arranged more than 11. This is because when the number is small, it is unable to successfully control temperature of each body portion.

The infrared ray irradiation sources are preferably arranged more than 3 rows particularly in the length (height) direction of the human body and more than 2 rows in the circumferential direction. In particular, the number of rows of infrared ray irradiation sources arranged in the circumferential direction is preferably increased for the breast and the abdomen, and reduced for the leg portion. For the leg portion, it is desirable to irradiate the leg portion with infrared rays also from the sole of the foot, and consequently, it is preferable to provide an infrared ray irradiation source on the sole side.

It is preferable to separate and space these plurality of infrared ray irradiation sources with aluminum reflection plates. Aluminum provides high reflection efficiency of far infrared rays and even when the same infrared rays irradiation sources are used, irradiation and treatment of better efficiency can be carried out.

In this invention, it is preferable to install a fan for ventilating and fluidizing the air layer in the said space portion. Because installing this fan can control the atmosphere around the human body comparatively uniformly and the surface portion can be set to low temperature with the inside temperature of the human body maintained high by irradiation of far infrared rays, burden to the patient can be reduced. Furthermore, humidity of the atmosphere around the human body can be controlled by ventilation and it is possible to freely set the low-humidity and high-humidity condition, thereby improving the treatment effects.

In addition, the other characteristic of the far infrared irradiation source according to this invention lies in that the irradiation source has a heat generator and an infrared ray irradiation member heated by this heat generator for radiating far infrared rays free of near infrared rays of wavelength less than 4 $\mu$m, and is designed to allow the heat generator to generate more heat at the peripheral portion rather than at the central portion of the infrared ray irradiation member.

With this configuration, the heating calorie at the peripheral portion with larger heat dissipation than at the central portion with less heat dissipation increases for the infrared ray irradiation member, and as a result, the temperature distribution of the infrared ray irradiation member becomes uniform, and far infrared rays can be radiated uniformly from the whole surfaces of the infrared ray irradiation member.

According to this invention, a far infrared ray irradiation source which can radiate only far infrared rays desirable for hyperthermia from the infrared ray irradiation members can be provided.

It is preferable that the said heat generator is composed with heating wires, and the installation density of the said heating wires is designed to be higher at the peripheral portion than at the central portion of the said infrared ray irradiation member.

BRIEF DESCRIPTION OF THE DRAWINGS

FIG. 6 is a top view partly broken away of the far infrared ray irradiation source shown in FIG. 5.

DETAILED DESCRIPTION OF THE PREFERRED EMBODIMENTS

Referring now to drawings, there are shown preferred embodiments of the infrared ray irradiation apparatus according to the present invention.

Figure 3:
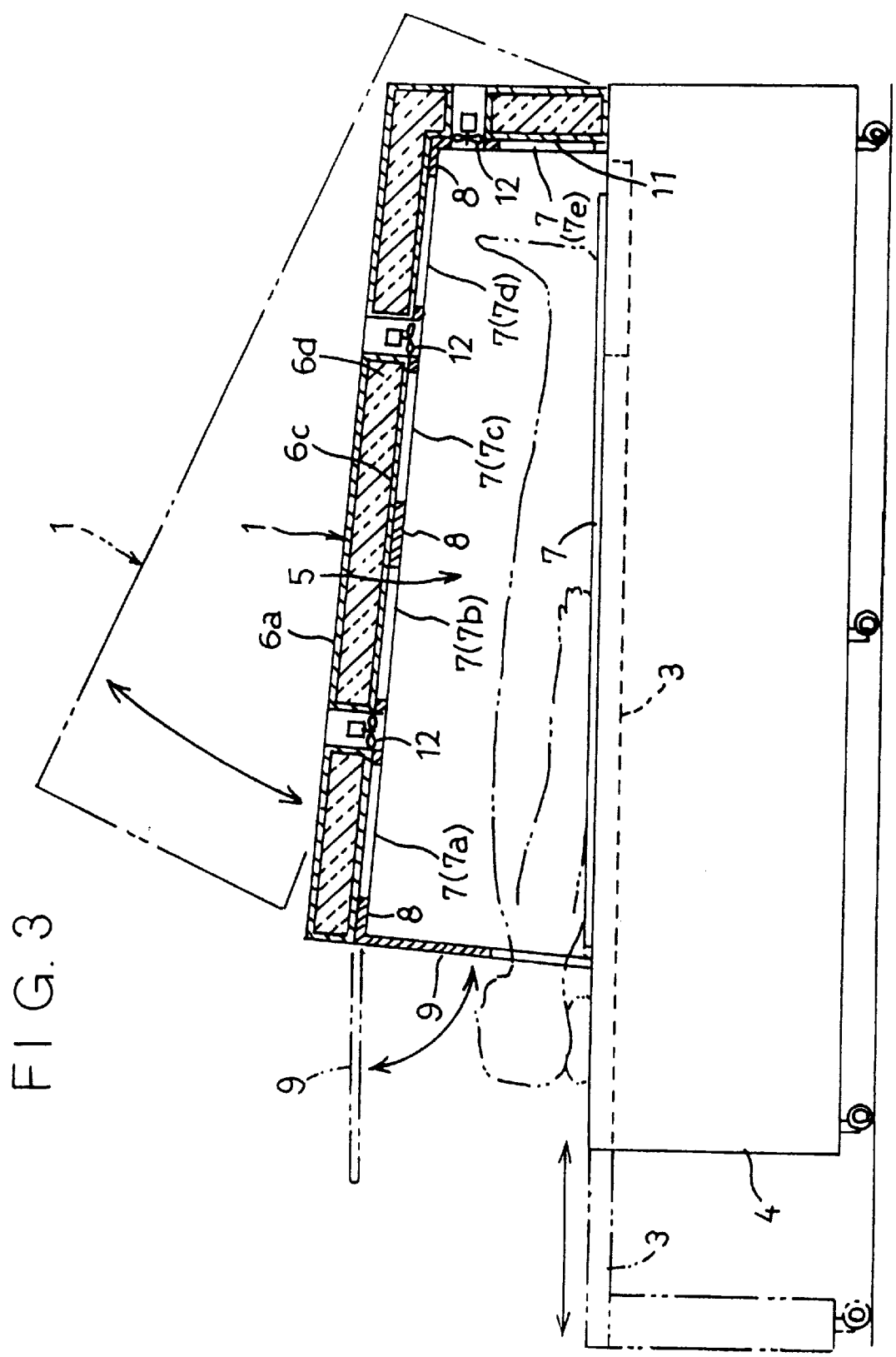
FIG. 3 shows one example of arrangement of a human body and heaters.

This infrared ray irradiation apparatus comprises a cover portion 1 and a bed portion 2. This bed portion 2 further comprises a human body mounting portion 3 and a base portion 4 for accommodating the human body mounting portion 3. The said cover portion 1 has a semi-cylindrical form, and a space 5 is formed for accommodating the human body by the human body mounting portion 3 and the cover portion 1. The base portion 4 can accommodate a power supply portion, a control portion, a device for monitoring and displaying patient condition, an oxygen supplying apparatus, etc. inside. The cover 1 can be opened and closed for accommodating and diagnosing the patient as well as installing necessary sensors. In addition, as shown in FIG. 3, it is preferably designed to open and close the end portion in the human body leg direction as an axis. It may be opened and closed by mechanical action using hydraulic cylinders, etc. or electrically or manually.

Next discussion will be made on the main apparatus portion for irradiating the human body with far infrared rays using this apparatus and carrying out treatments of diseases, etc.

Figure 4:
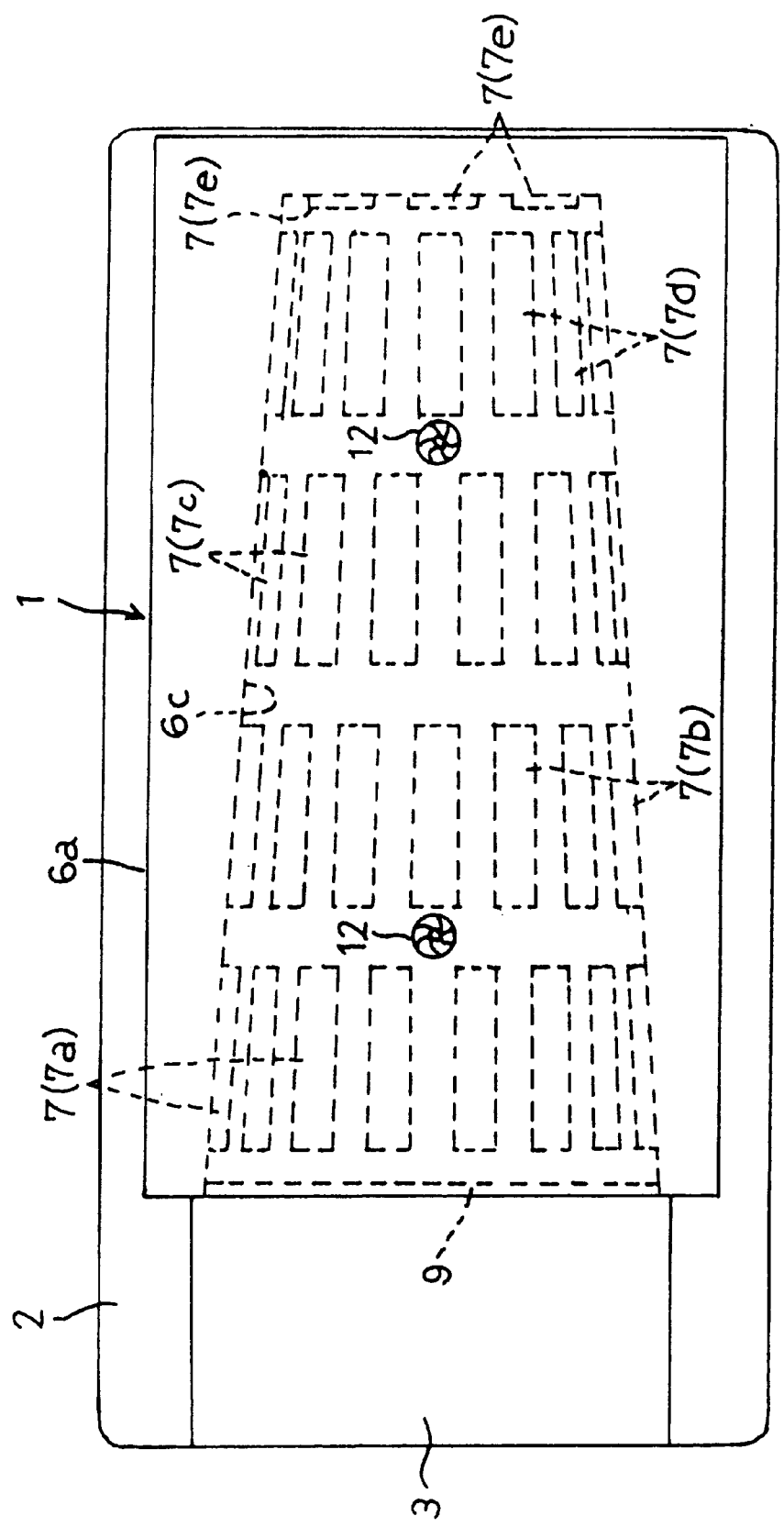
FIG. 4 shows one example of heaters arranged on the interior panel.

This portion has a nearly flat human body mounting portion 3 for forming a space 5 to accommodate the lying human body and a semi-cylindrical cover portion 1 arranged around the human body. The space 5 for accommodating the human body is nearly semi-cylindrical, with one end equipped with a head portion isolating cover 9 which isolates the space S from the outside at the neck portion of the human body. To the leg side of the human body, a leg portion isolating cover 11 is installed. Of the said cover portion 1, on the side facing the space 5 of the human body mounting portion 3 and the cover portion 1, a plurality of infrared irradiation sources 7 (7a–7e) are placed for irradiating far infrared rays not containing near infrared rays of wavelength less than 4 $\mu$m as shown in FIG. 4. The space 5 is designed with various sizes of the patient as well as the motion of the patient inside taken into account. If the human body surface is too distant from the infrared ray irradiation source, attenuation of far infrared rays increases.

Figure 1:
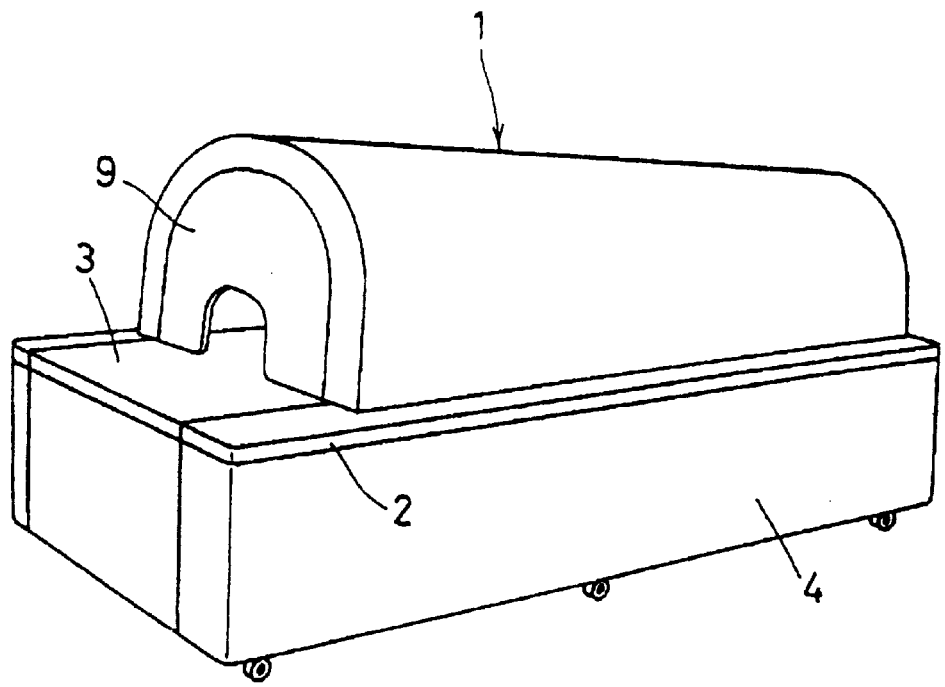
FIG. 1 is a whole view schematically showing the infrared ray irradiation apparatus.
Figure 2:
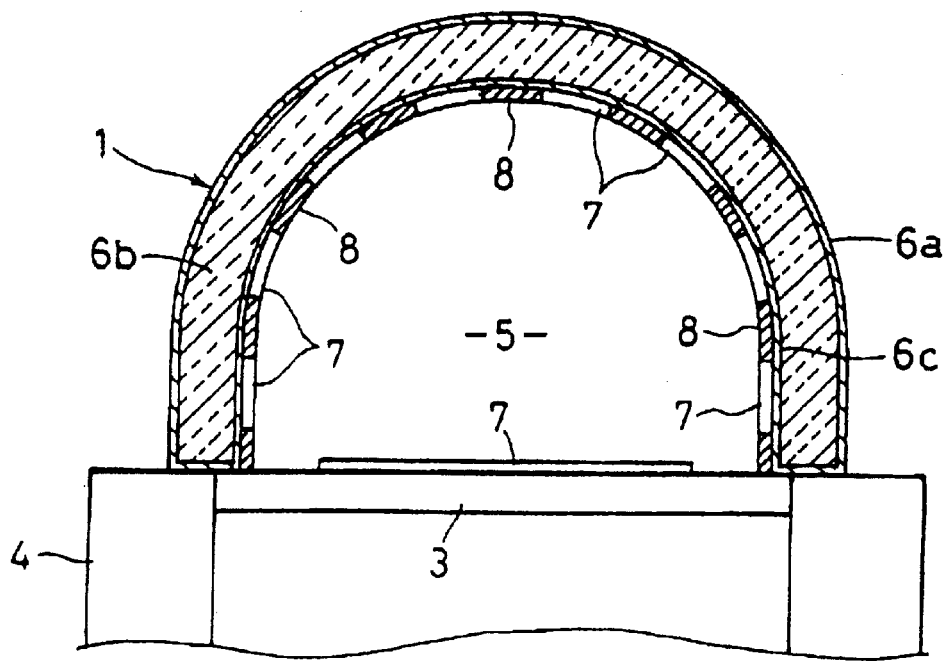
FIG. 2 shows the space for accommodating a human body and irradiating the human body with far infrared rays as seen from the head direction of the human body.

The cover portion 1 comprises an exterior member 6a, interior panel 6c, and material containing filling member 6b placed in-between as shown in FIG. 2. The filing material 6b is preferably heat-insulating material. On the interior panel 6c, the infrared ray irradiation source is placed in such a manner that the irradiating surface sufficiently faces the human body. The power supply cord connected to the infrared ray irradiation source 7 is preferably installed in the heat-insulating material layer and connected to the power supply portion and control portion.

The head isolating cover 9 is installed to the cover portion 1 free to open and close, and even if any unforseeable incident such as power failure, etc. occurs, it is desirable to be designed to move the patient outside the apparatus.

Consequently, it is convenient for the head isolating cover 9 to be installed free to open and close, and may be formed with two or more members. In the illustrated example, the head isolating cover is installed free to open and close upwards. The head isolating cover 9 may be formed in part or in whole with transparent substrate so that the inside can be seen.

On the surface of the interior panel 6c between infrared ray irradiation sources, a reflection member 8 for reflecting far infrared rays is installed. This reflection member 8 is metal, preferably aluminum (including pure aluminum and aluminum alloy) or a substrate covered with aluminum. Examples of a method to use the interior panel surface between infrared ray irradiation sources for the reflection member include (a) a method for forming a recess or hole on the interior panel, and fitting and mounting the infrared ray irradiation source, (b) a method for mounting the infrared ray irradiation source to the interior panel component member different from the reflection member and mounting the reflection member around it, and (c) a method for forming the interior panel with aluminum plate and on this panel, installing the infrared ray irradiation source via insulators, heat insulators, etc. of the nearly same profile of the infrared ray irradiation source as required.

The infrared ray irradiation source used for this apparatus has heater members and ceramic members, and these ceramic members are formed in such a manner to be fitted to the heater members so that they work to shield near infrared rays of wavelength less than 4 μm generated from the heater members or to convert them to far infrared rays. As a result, the infrared ray irradiation source used for this apparatus does not emit near infrared rays of wavelength less than 4 μm. However, in general, the infrared ray irradiation source has a wavelength distribution in emitted infrared rays, and the probability to contain near infrared rays increases as temperature rises. The infrared ray irradiation source used for this apparatus is no exception, and therefore, the infrared ray irradiation source of this apparatus has the wavelength distribution of emitted infrared rays set to the long wavelength side and at the same time, the heater capacity set to the level required for treatment but to the level that does not allow it to contain near infrared rays.

For the ceramic members, zirconia-system, alumina-system, and other materials are known, and any of them which can shield near infrared rays of wavelength less than 4 μm is applicable, but it is desirable to use the material 2 mm or more in thickness.

The human body mounting portion 3 also has the infrared ray irradiation source which does not irradiate near infrared rays of wavelength less than 4 μm. The said infrared ray irradiation source may be composed of a plurality of sources or a single source. The human body mounting portion 3 is designed to be formed to slide to the base portion 4 and to be drawable. Consequently, it is desirable for casters to be equipped. Allowing the human body mounting portion 3 to be slid and drawn out in this way, the patient can be easily transferred between the stretcher and the infrared ray irradiation apparatus.

The cover portion 1 is formed nearly in a semi-cylindrical profile at the portion forming the space 5, but it is desirable that the human leg side is designed to be formed in a smaller radius.

In the space 5, it is preferable to install two or more fans 12. Installing two or more fans in this way can maintain the air inside the space to uniform temperature even when a specific portion of the human body is irradiated intensively.

The temperature inside the space 5 should be preferably on the order of 50–80° C., more suitably, from 55–65° C.

The human body is irradiated with far infrared rays with the head protruded from space 5 to the outside, and the head is preferably cooled during irradiation. Consequently, the head mounting member is preferably designed to be cooled.

The human body is irradiated and treated with one or more sensors equipped. The sensor is supposed to measure temperature of each portion of human body, blood pressure, heart rate, and others which are necessary to check the patient condition. In particular, temperature inside the human body must be measured, and for example, temperature of stomach and rectum should be suitably measured.

This infrared ray irradiation apparatus can be controlled by increasing the intensity of irradiation source to rapidly raise the human body temperature to the specified level at the initial stages of irradiation treatment. By achieving this kind of configuration, treatment time can be shortened and the number of patients per apparatus can be increased.

EXAMPLE

To the interior panel 6c, a total of 11 or more pieces of far infrared ray irradiation sources with the infrared ray irradiation surface measuring 10 cm by 23 cm are arranged, namely, 4 or more of them are provided around the breast portion of the human body, 4 or more of them are provided around the abdomen portion, 2 or more of them are provided to the upper leg portion, and one of them is provided to the lower leg portion, as well as one piece measuring 52 cm by 1580 cm to the human body mounting portion 3.

The heater capacity used for each infrared ray irradiation source is shown as follows:

Heater used for infrared ray irradiation source on interior panel 6c: 300 W

Heater used for infrared ray irradiation source on human body mounting portion: 150 W The reason why the heater capacity used for the human body mounting portion 3 is smaller is that the human body makes direct contact with the human body mounting portion (cushioning material is used as required), and when the distance between the infrared ray irradiation source and the human body is short and attenuation is small, and a small-capacity heater is sufficient. In FIG. 3, an infrared ray irradiation source arranged in parallel to the cylindrical shaft is shown, but it is not necessarily arranged in parallel but each infrared ray irradiation source may be rotatably equipped. The temperature inside the space 5 is set to 60° C.±5° C.

ANOTHER EMBODIMENT

Figure 5:
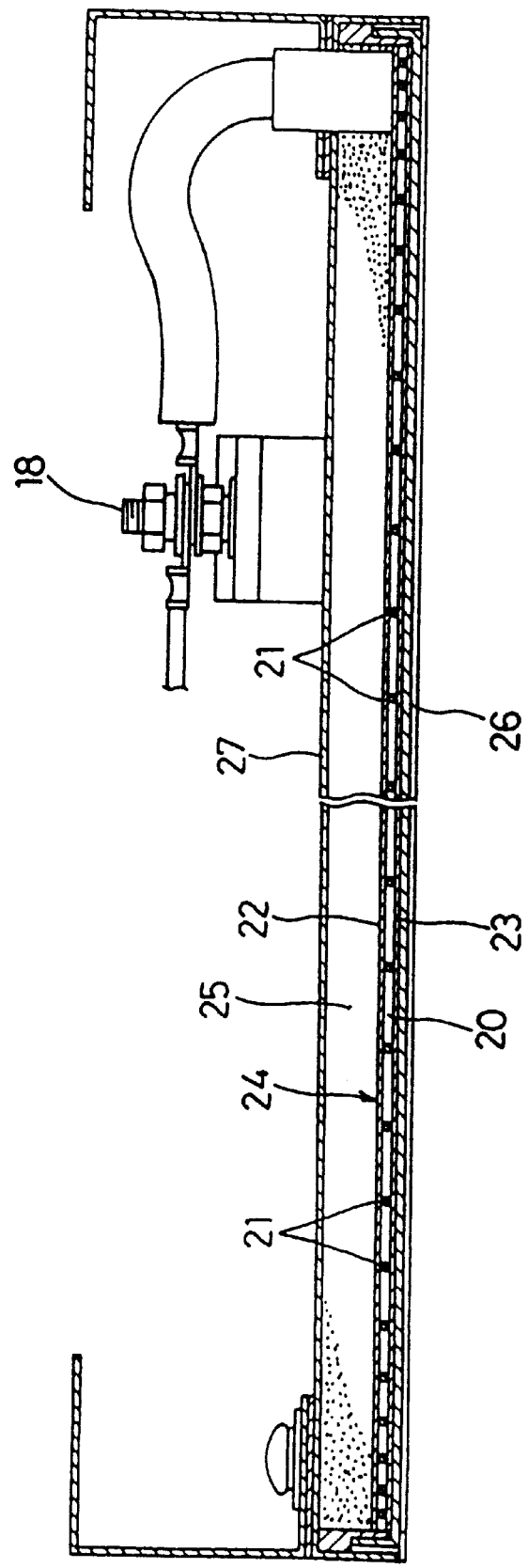
FIG. 5 is a cross-sectional view of the other embodiment of the far infrared ray irradiation source used for the infrared ray irradiation apparatus according to this invention.

For the infrared ray irradiation source, those with construction as shown in FIG. 5 and FIG. 6 may be used. That is, this infrared ray irradiation source comprises a heat generator and an infrared ray irradiation member for being heated with this heat generator and emitting far infrared rays, as well as the heat generation rate by the said heat generator is designed to increase more at the circumferential portion than at the center portion of the said infrared ray irradiation member.

This far infrared ray irradiation source holds and supports the heat generator 24 with both surfaces covered with insulator 22, 23 by repeating operation to reciprocately placing heating wire 21 from one edge to the other edge in the shorter direction of the heater substrate 20 comprising rectangular mica sheets, etc. along the longitudinal direction as shown in FIG. 5 and FIG. 6 together with the irradiation sheet 26 formed with the insulating plate 25 of the same rectangle and alumina-system ceramics as infrared ray irradiation member. It is built by being fixed with a retainer plate 27 from the above and mounting a lead terminal 18 for feeding power to the heating wire 21 on the insulating plate 25 side.

In this case, by setting the intervals of heating wires placed nearly in parallel along the shorter direction of the heater substrate 20 narrower in the vicinity of both edge portions in the longitudinal direction and wider towards the central portion, it is possible to configure that the heat generation rate by the said heat generator is increased at the circumferential portion than at the central portion of the infrared ray irradiation member. Needless to say, the intervals of heating wires 21 narrowed in the vicinity of both edge portions in the longitudinal direction may be provided on one edge portion only.

For the arrangement of heating wires, in addition to the above arrangement or separately from the above arrangement, the intervals of heating wires may be narrowed in the vicinity of both edge portions in the shorter direction of the heater substrate 20 and widened towards the central portion side.

What is claimed is:

1. An infrared ray irradiation apparatus comprising:

a base portion;

a human body mounting portion which is slidably pushed in or pulled out from the base portion;

an operable cover portion which is provided on the base portion and is comprised of an exterior member, an interior panel and a member containing filling material provided between said exterior member and said interior member; and a plurality of far infrared ray irradiation sources for irradiating far infrared rays not containing near infrared rays of wavelength less than 4 $\mu$m and having a irradiation intensity controlled to raise the temperature of a human body to a desired level, wherein said far infrared irradiation sources are provided at positions close to a portion of the human body to be irradiated so that a whole human body accommodated in a space formed by said human body mounting portion and said operable cover portion can be uniformly heated to a desired temperature without causing any low temperature burns.

2. An infrared irradiation apparatus according to claim 1, wherein each of the plurality of far infrared ray irradiation sources is allowed to independently control the infrared ray irradiation intensity.

3. An infrared ray irradiation apparatus according to claim 1, wherein eleven or more far infrared irradiation sources are provided.

4. An infrared ray irradiation apparatus according to claim 1, wherein an aluminum reflecting plate is provided between the adjacent infrared ray irradiation sources.

5. An infrared ray irradiation apparatus according to claim 1, wherein a fan is provided for ventilating and fluidizing an air layer inside the space formed by said human body mounting portion and said operable cover portion.

6. An infrared irradiation apparatus according to claim 1, wherein a far infrared irradiation source is mounted on said human body mounting portion.

7. An infrared irradiation apparatus according to claim 1, wherein a reflection member is provided between two adjacent infrared irradiation sources.

8. An infrared irradiation apparatus according to claim 7, wherein said reflection member between said infrared irradiation sources is made of aluminum or aluminum alloy.

9. An infrared irradiation apparatus according to claim 7, wherein a fan is provided on the operable cover portion for ventilating said space formed by said human body mounting portion and said operable cover portion.

10. An infrared ray irradiation apparatus comprising:

a base portion;

a human body mounting portion being drawable by sliding along the base portion;

an operable cover portion comprising an exterior member, interior panel, a member containing filling material provided between said exterior member and said interior member, and a head isolating cover provided at an end of the operable cover portion in such a way that a head portion of the human body is not exposed to the infrared ray; and a plurality of infrared ray irradiation sources for irradiating far infrared rays not containing near infrared rays of wavelength less than 4 $\mu$m;

wherein said infrared ray irradiation sources are aligned in a plurality of rows in a lengthwise direction of the operable cover portion.

* * * * *